United States Patent [19]

Junghans

[11] 4,194,046

[45] Mar. 18, 1980

[54] PREPARATION OF 4,4'-DIPYRIDYLS

[75] Inventor: Klaus Junghans, Berlin, Fed. Rep. of Germany

[73] Assignee: Schering Aktiengesellschaft, Berlin and Bergkamen, Fed. Rep. of Germany

[21] Appl. No.: 20,675

[22] Filed: Mar. 15, 1979

[30] Foreign Application Priority Data

Mar. 15, 1978 [DE] Fed. Rep. of Germany ....... 2811803

[51] Int. Cl.$^2$ .......................................... C07D 213/22
[52] U.S. Cl. .................................... 546/259; 546/260
[58] Field of Search ............................... 546/259, 260

[56] References Cited

U.S. PATENT DOCUMENTS

| 3,210,364 | 10/1965 | Campbell et al. | 546/259 |
| 3,210,367 | 10/1965 | Bradbury et al. | 546/260 |
| 3,491,104 | 1/1970 | Colchester et al. | 546/260 |

FOREIGN PATENT DOCUMENTS 1913150  3/1969  United Kingdom ..................... 546/260

OTHER PUBLICATIONS

Chem. Abstracts, vol. 79, Abst. No. 126,326k (1973) (abst. of U.S.S.R. 387,991).
Beck, Elektoro-Organische Chemie, p. 166, 1974.

Primary Examiner—John D. Randolph
Attorney, Agent, or Firm—Millen & White

[57] ABSTRACT 4,4'-Dipyridyls are produced by electrolysis of 4-unsubstituted pyridines in liquid ammonia containing a conducting salt, e.g., salts of tetraalkylammonium, alkali metal and alkaline earth metals, for example potassium chloride.

11 Claims, No Drawings

PREPARATION OF 4,4'-DIPYRIDYLS

BACKGROUND OF THE INVENTION

This invention relates to the preparation of 4,4'-dipyridyls.

It is known that the electrolytic reduction of pyridine in aqueous dilute sulfuric acid yields piperidine, with a yield of over 90%. By-products of this process are 2,2'- and 4,4'-dipyridyl, both produced in minor amounts [F. Beck, "Elektro-organische Chemie" (Electroorganic Chemistry): 166, Chemie Publishers, 1974].

It is also known that 4,4'-dipyridyl can be produced by reacting pyridine with metallic sodium at about 100° C. (e.g., U.S. Pat. Nos. 3,210,364; 3,210,367).

Furthermore, 4,4'-dipyridyl can be produced by the reaction of pyridine with metallic sodium in liquid ammonia in the presence of a large excess of dimethylformamide (Dutch Pat. No. 6,603,415).

However, the heretofore known processes for the production of 4,4'-dipyridyl are characterized by low yields and they can only be conducted with special safety precautions, because metallic sodium is used in most of the prior art processes.

Accordingly, it is a principal object of the present invention to provide a better process for the production of 4,4'-dipyridyls.

An additional object of this invention is to provide such a process which is relatively simple, safe, and economical.

A further object is to provide electrolytic bath compositions used in the process of the invention.

Upon further study of the specification and appended claims, further objects and advantages of this invention will become apparent to those skilled in the art.

SUMMARY OF THE INVENTION

Such objects of this invention are achieved by conducting an electrolysis of a 4-unsubstituted pyridine, including mixtures, if desired, in a liquid ammonia electrolyte containing a conducting salt in order to produce the desired 4,4'-dipyridyls.

DETAILED DISCUSSION

It is to be understood that all 4-unsubstituted pyridines are useful starting materials, but of course any substituted moieties on the pyridine nucleus should not deleteriously interfere with the formation of the 4,4'-dipyridyls. Interfering moieties have not yet been found, however, and therefore the presence of such moieties is only speculative.

Preferred starting materials are pyridine and 4-unsubstituted alkylpyridines. The term "4-unsubstituted alkylpyridines" designates alkylpyridines substituted in the 2-, 3-, 5- or 6-position by one or more alkyl groups of 1-6, preferably 1-3, most preferably 1-2, carbon atoms, e.g., α-picoline, β-picoline, 2,6-dimethylpyridine, 2.3.5-trimethylpyridine and 2-ethyl-5-methylpyridine.

Similarly, the term "alkyl-substituted 4,4'-dipyridyls" designates 4,4'-dipyridyls substituted by the same alkyl groups as the 4-unsubstituted alkylpyridines in the 2-, 3-, 5- or 6-position, respectively, on the dipyridyl rings.

4,4'-Dipyridyl and the alkyl-substituted 4,4'-dipyridyls which are produced by the electrolysis process of this invention are used as the starting materials in the conventional manufacture of herbicides, e.g., "Paraquat". For further details, attention is invited to: Kirk-Othmer, Encyclopedia of Chemical Technology, 2nd edition, Vol. 22, p. 207–209.

Liquid ammonia serves as the electrolyte as well as the solvent for the electrolysis conducted according to this invention.

The conducting salts present in the electrolyte enable the passage of the electric current in the solution and must be soluble and dissociated in liquid ammonia to be effective. The solution may be saturated with the conducting salts, even an undissolved excess does not interfere with the reaction.

Suitable conducting salts include, but are not limited to, salts of tetraalkylammonium, alkali metal, alkaline earth metals, whose anions do not affect the course of the electrolysis, i.e., the anions do not participate in the reactions taking place during the electrolysis, other than to conduct the current.

The conducting salts present in the electrolyte are preferably salts of strong acids. Examples of suitable anions are perchlorate, tetrafluoroborate, halogenides, such as chloride and bromide, p-toluenefulfonate or hexafluorophosphate.

Examples of preferred salts include, but are not limited to: tetraethylammonium perchlorate, methyltriethylammonium p-toluenesulfonate; sodium chloride, bromide and perchlorate, p-toluenesulfonate and hexafluorophosphate; and the corresponding potassium salts.

The conducting salts are used of course in conducting amounts, preferably in the amount of 0.01 to saturation, and especially 0.1 to 3 gram equivalents per liter of liquid ammonia.

The amount of starting 4-unsubstituted pyridine per liter of ammonia can vary very widely according to conventional electrolysis procedures. In any case, the following table in column I shows a preferred electrolyte composition at the beginning of the electrolysis, and in column II, a preferred electrolyte composition at the end of the reaction.

|  | Electrolyte Composition | |
|---|---|---|
|  | I. Initial | II. Final |
| Liquid ammonia | 1 liter | 1 liter |
| Conductive Salt | 0.1 to 3 gm. equivalent | 0.1 to 3 gm. equivalent |
| 4-unsubstituted pyridine | 0.1 to 3 gm. mole | 0.03 to 1 gm. mole |
| 4,4'-dipyridyl | 0 | 0.06 to 1,5 gm. mole |

Current density has no direct effect on the course of the electrolysis according to this invention; it generally ranges from 1 to 50 amperes/dm$^2$.

Electrodes used in the electrolysis process of this invention can be made from any conventional materials so long, of course, as the electrodes remain stable under the electrolysis conditions. A suitable cathode material is, for example, aluminum, stainless steel, titanium, platinum and vitreous carbon. Stainless steel is generally preferred. A suitable anode material is, for example, graphite, vitreous carbon and noble metals, such as platinum. Graphite is generally preferred.

The electrolysis of this invention is usually conducted under atmospheric pressure at a temperature of from −70° C. up to the normal boiling point of the reaction mixture. Even higher temperatures can also be employed, but at the higher temperatures the reaction must be conducted under super-atmospheric pressures.

The electrolysis is conducted under substantially anhydrous conditions, preferably having no more than 1 gram of water per liter of liquid ammonia.

The electrolysis is ordinarily conducted without auxiliary solvents. However, as will be obvious to those skilled in the art, the electrolysis can also be conducted in the presence of commonly known auxiliary solvents, e.g., tetrahydrofuran or dimethylformamide in addition to the ammonia.

As will also be apparent to those skilled in the art, the electrolysis can be conducted either by adding the starting material, a 4-unsubstituted pyridine, dropwise to the electrolyte solution of ammonia and the conducting salt in the electrolytic cell; or, by adding the entire amount of the starting material to the electrolytic cell, filled with liquid ammonia and the conducting salt before the beginning of the process.

The electrolysis can be conducted either in a divided, or in an undivided cell. As will be further apparent to those skilled in the art, in the divided cell, diaphragms and/or ion exchange membranes used to divide the cell are made from conventional porous materials. Examples of such diaphragms or membranes are sintered clay dividers and sintered glass dividers.

When the electrolysis is conducted in an undivided electrolytic cell, the product of the reaction is recovered by evaporating the electrolyte (ammonia); distilling off the residual starting materials and extracting the 4,4'-dipyridyl from the residue with a suitable solvent, such as diisopropyl ether, or any other solvent selective for the 4,4'-dipyridyl involved.

If the electrolysis is conducted in a divided cell, the product is recovered by evaporating the catholyte (ammonia); distilling off the residual starting materials, and extracting the 4,4'-dipyridyl from the residue with the same solvent as set forth above for the electrolysis in the undivided cell.

The yield of the recovered 4,4'-dipyridyl in both processes (the divided and the undivided cell) is generally about at least 50%, preferably at least 30%.

The process can be conducted either batchwise or as a continuous reaction. The electrolysis process is conventional.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

10 g. of pyridine is electrolyzed in 250 ml. of liquid ammonia and 1 g. of sodium bromide in a cell divided by a sintered glass plate with the use of an aluminum cathode and an anode of vitreous carbon, at a current density of 1 amperes/dm$^2$ for three hours. After the catholyte has been evaporated in the air, 7 g. of pyridine is obtained by distillation. Extraction of the residue with diisopropyl ether yields 1.3 g. of 4,4'-dipyridyl, m.p. 110°–112° C.

EXAMPLE 2

10 g. of pyridine is electrolyzed for two hours in 200 ml. of liquid ammonia with 3 g. of tetraethylammonium perchlorate in an undivided cell between a titanium cathode and a graphite anode at 10 amperes/dm$^2$. After the ammonia has been evaporated in air, distillation yields 7.5 g. of pyridine. After extraction of the residue with diiospropyl ether, 1.0 g. of 4,4'-dipyridyl is obtained, m.p. 109°–110° C.

EXAMPLE 3

5 g. of α-picoline is electrolyzed for three hours in 250 ml. of liquid ammonia in the presence of 2 g. of sodium perchlorate in a cell divided by a cation exchange membrane between a stainless steel cathode and an anode of vitreous carbon, at a current density of 10 amperes/dm$^2$. After the catholyte has been evaporated in air, 3 g. of unreacted α-picoline is obtained, along with 0.6 g. of 2,2'-dimethyl-4,4'-dipyridyl, m.p. 85°–86° C.

EXAMPLE 4

10 g. of pyridine is added dropwise to 200 ml. of liquid ammonia and 1 g. of potassium chloride during electrolysis between a stainless steel cathode and a vitreous carbon anode at 20 amperes/dm$^2$. After the pyridine has been added, the electrolyte is allowed to evaporate in air at room temperature. After 7 g. of pyridine has been distilled off, extraction of the residue with diisopropyl ether yields 1.8 g. of 4,4'-dipyridyl, m.p. 110°–111° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of a 4,4'-dipyridyl by electrolysis of a 4-unsubstituted pyridine the improvement which comprises carrying out the electrolysis in liquid ammonia containing a conducting salt.

2. A process according to claim 1, wherein the conducting salt is selected from the group consisting of tetraalkylammonium, alkali metal and alkaline earth metal salts of strong acids.

3. A process according to claim 2, wherein 4,4'-dipyridyl is produced from pyridine.

4. A process according to claim 3 wherein the conducting salt is an alkali metal salt of a strong acid.

5. A process according to claim 4 wherein the conducting salt is an alkali metal perchlorate, tetrafluoroborate, halogenide, p-toluenesulfonate or hexafluorophosphate.

6. A process according to claim 5 wherein the conducting salt is potassium chloride.

7. A process according to claim 5 wherein the conducting salt is sodium bromide.

8. A process according to claim 3 wherein the conducting salt is tetraethylammonium perchlorate.

9. A process according to claim 2 wherein 2,2'-dimethyl-4,4'-dipyridyl is produced from α-picoline.

10. A process according to claim 9 wherein the conducting salt is sodium perchlorate.

11. An electrolytic bath composition comprising liquid ammonia, a conducting salt and a 4-unsubstituted pyridine.